(12) United States Patent
Siegal et al.

(10) Patent No.: US 9,662,222 B2
(45) Date of Patent: May 30, 2017

(54) MEDICAL DEVICE LOCK MECHANISM

(71) Applicant: NLT SPINE LTD, Kfar Saba (IL)

(72) Inventors: Tzony Siegal, Moshav Shoeva (IL); Dvir Keren, Tel Aviv (IL); Oded Loebl, Tel Mond (IL); Didier Toubia, Raanana (IL)

(73) Assignee: NLT SPINE LTD, Kfar Saba (IL)

( * ) Notice: Subject to any disclaimer, the term of this patent is extended or adjusted under 35 U.S.C. 154(b) by 117 days.

(21) Appl. No.: 14/664,867

(22) Filed: Mar. 22, 2015

(65) Prior Publication Data

US 2015/0209151 A1    Jul. 30, 2015

Related U.S. Application Data

(63) Continuation of application No. 13/579,292, filed as application No. PCT/IB2011/050648 on Feb. 16, 2011, now Pat. No. 9,017,408.

(Continued)

(51) Int. Cl.
*A61F 2/44* (2006.01)
*A61F 2/02* (2006.01)
(Continued)

(52) U.S. Cl.
CPC .......... *A61F 2/44* (2013.01); *A61F 2/02* (2013.01); *A61F 2/4455* (2013.01); *A61B 17/7094* (2013.01); *A61B 17/8852* (2013.01); *A61F 2002/2835* (2013.01); *A61F 2002/3052* (2013.01); *A61F 2002/30331* (2013.01); *A61F 2002/30367* (2013.01); *A61F 2002/30462* (2013.01); *A61F 2002/30469* (2013.01); *A61F 2002/30522* (2013.01); *A61F 2002/30624* (2013.01); *A61F 2002/30632* (2013.01); (Continued)

(58) Field of Classification Search
CPC ............................................... A61F 2002/4415
USPC ........................................... 623/17.11–17.16
See application file for complete search history.

(56) References Cited

U.S. PATENT DOCUMENTS

| 7,785,368 B2 | 8/2010 | Schaller |
| 7,947,078 B2 | 5/2011 | Siegal |

(Continued)

FOREIGN PATENT DOCUMENTS

| IL | WO2006072941 | 7/2006 |
| WO | 2008103832 | 2/2008 |
| WO | WO2008103781 | 8/2008 |
| WO | WO2008103832 | 8/2008 |

*Primary Examiner* — David Bates
(74) *Attorney, Agent, or Firm* — Mark M. Friedman

(57) ABSTRACT

A medical device (10) includes an implant body (20) with a number of segments (30) hingedly interconnected so as to assume a straightened state for delivery and a flexed or roughly curved deployed state. Implant body may have engagement elements on at least two different segments, for example on a majority of segments. An elongated locking element anchored at the distal segment of the implant body may have projections for at least each engagement element. Tension applied to the locking element biases the implant body from the straightened state to the flexed deployed state. When the locking element is deflected to reach the curved deployed state, flexing segments of the implant body lock by matching engagement elements of the implant body with projections of the locking element. A very secure lock may be formed to prevent opening after deployment.

19 Claims, 9 Drawing Sheets

Related U.S. Application Data

(60) Provisional application No. 61/304,857, filed on Feb. 16, 2010.

(51) Int. Cl.
 *A61B 17/70* (2006.01)
 *A61B 17/88* (2006.01)
 *A61F 2/28* (2006.01)
 *A61F 2/30* (2006.01)
 *A61F 2/46* (2006.01)

(52) U.S. Cl.
 CPC . *A61F 2002/448* (2013.01); *A61F 2002/4415* (2013.01); *A61F 2002/4635* (2013.01); *A61F 2220/0025* (2013.01); *A61F 2220/0033* (2013.01); *A61F 2220/0075* (2013.01)

(56) References Cited

U.S. PATENT DOCUMENTS

| | | |
|---|---|---|
| 8,021,429 B2 | 9/2011 | Viker |
| 8,025,697 B2 | 9/2011 | McClellan, III et al. |
| 2007/0162135 A1 | 7/2007 | Segal et al. |
| 2008/0221687 A1* | 9/2008 | Viker .................. A61F 2/4455 623/17.16 |
| 2008/0234687 A1 | 9/2008 | Scaller et al. |
| 2008/0234827 A1 | 9/2008 | Schaller et al. |
| 2008/0249628 A1 | 10/2008 | Altarac et al. |
| 2008/0312743 A1 | 12/2008 | Vila et al. |
| 2009/0012612 A1 | 1/2009 | White et al. |
| 2010/0158969 A1 | 6/2010 | Tice |
| 2010/0198263 A1 | 8/2010 | Siegal et al. |
| 2013/0110239 A1 | 5/2013 | Siegal et al. |

\* cited by examiner

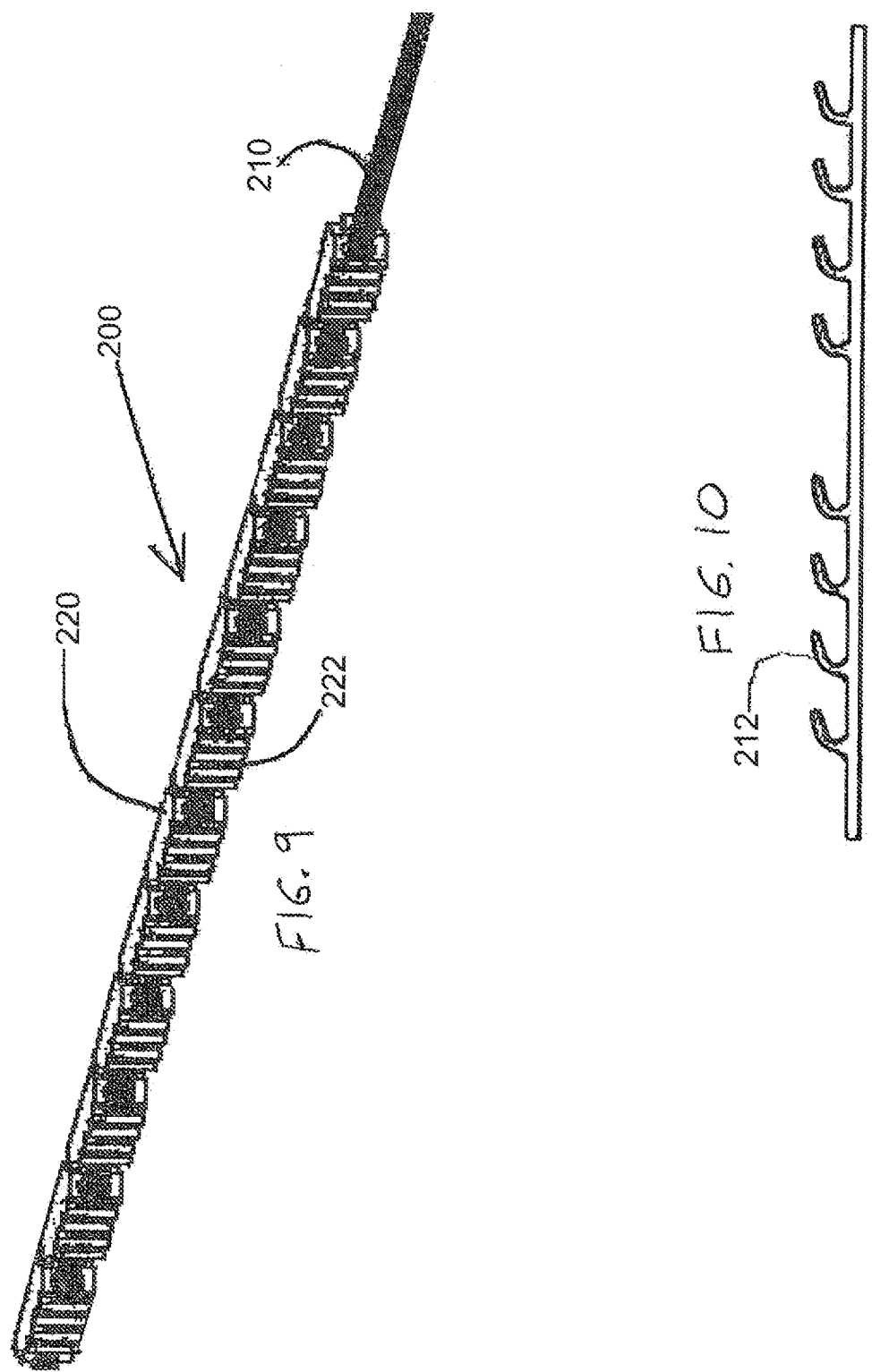

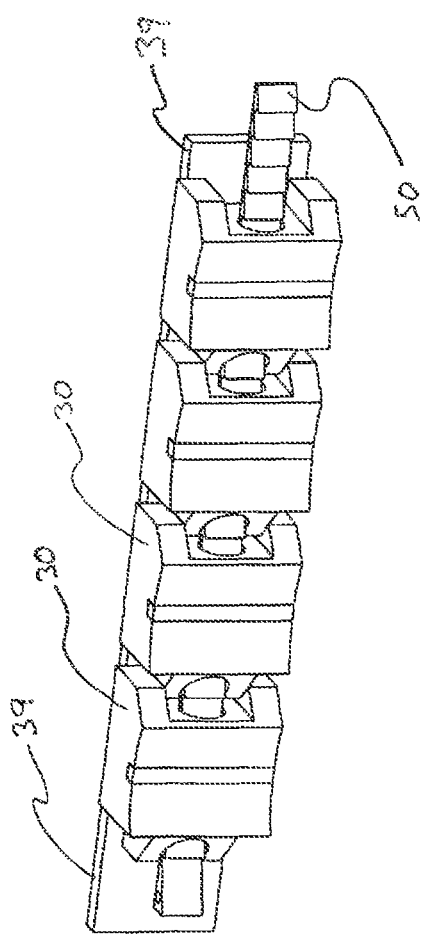
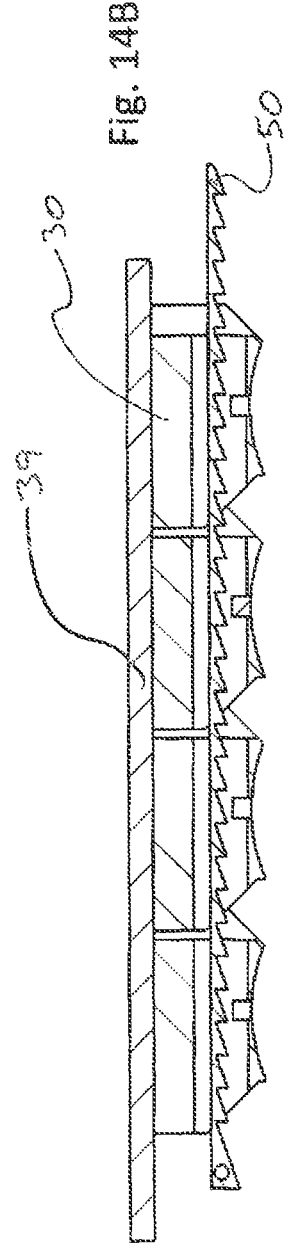

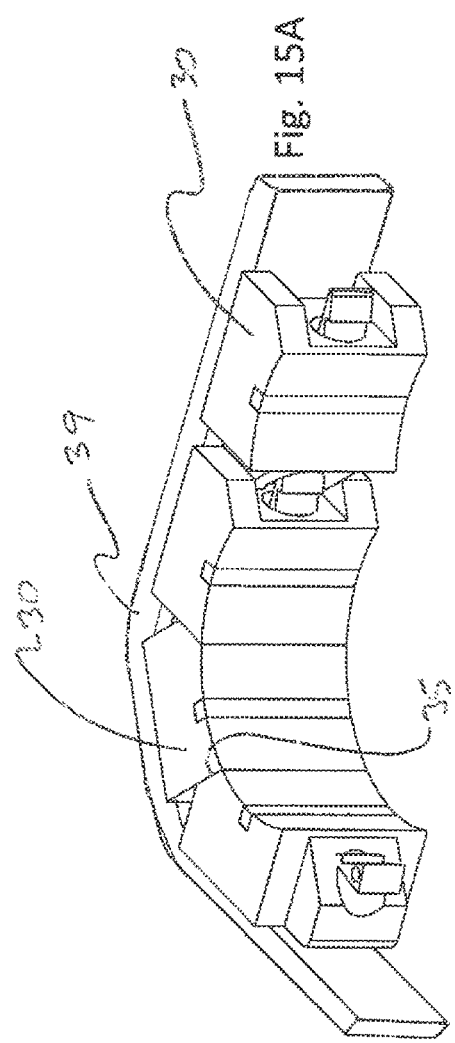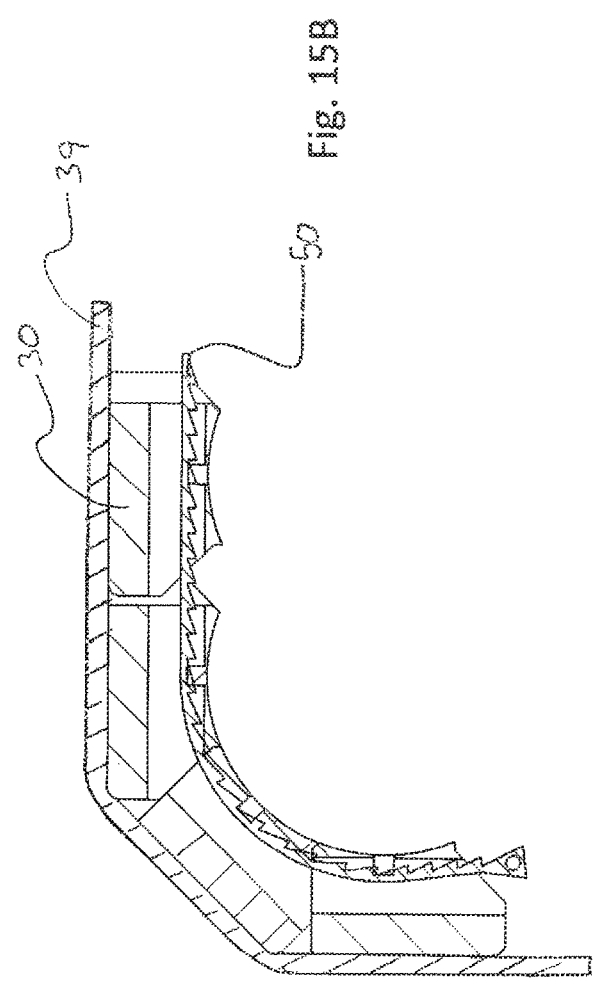

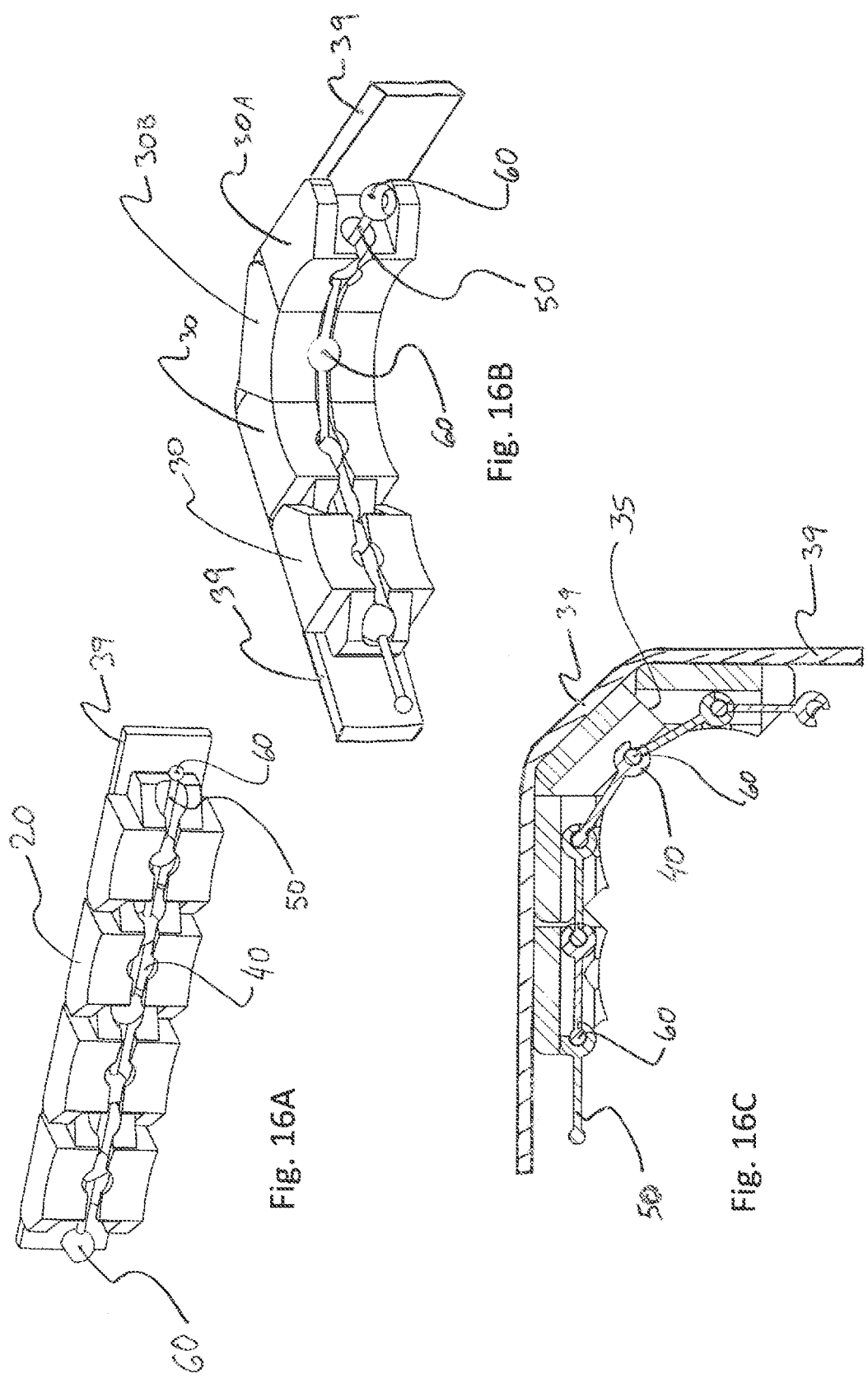

MEDICAL DEVICE LOCK MECHANISM

The present invention claims priority to U.S. provisional patent application No. 61/304,857 filed 16 Feb. 2010 by Applicant Siegal.

FIELD AND BACKGROUND OF THE INVENTION

The present invention relates to implant bodies, such as for spinal surgery and, in particular, it concerns an implant device having a very stable locking arrangement to prevent the implant body from opening up once implanted into the body.

Various devices have been proposed for implants and their deployment inside the spine or other parts of the body. An important feature of an implant is that it not only be delivered effectively but that it remain in position after deployment and not open in the body. Stability and a secure and reliable placement of the implant are critical. If the implant were to open after deployment, it could damage surrounding tissue and undo the effects of the spinal surgery.

PCT patent application publication no. WO 2009/019669 of Applicant published 12 Feb. 2009 teaches an implant including an implant body and an elongated tightening element that is introduced into a body in a straightened configuration and then assumes a roughly curved configuration within the body. The aforementioned publication is hereby incorporated by reference herein in its entirety.

It would therefore be highly advantageous to provide an implant (and associated method) that will not open in the body after deployment, for example for spinal surgery.

SUMMARY OF THE INVENTION

In accordance with one aspect of the present invention, there is provided a medical device comprising (a) an implant body including a plurality of segments interconnected so as to assume a straightened state and a flexed deployed state, the implant body formed with at least two engagement elements, each of at least two different segments having an engagement element; and (b) an elongated locking element anchored at one segment of said implant body, the locking element having at least two projections corresponding to the at least two engagement elements, wherein said implant body and said locking element are configured to lock, such that when said locking element is deflected to reach said flexed deployed state, the at least two projections of the locking element engage and lock with the at least two engagement elements of the implant body, each locking segment remaining locked after successive segments flex and lock, said locking arrangement being effective to lock said locking element relative to said implant body, thereby retaining said implant in said flexed deployed state.

A further aspect of the present invention is a medical device, comprising
(a) an implant body including a plurality of segments interconnected so as to assume a straightened state and a flexed deployed state, the implant body having at least two sockets, each of at least two different segments having a socket; and
(b) an elongated locking element anchored at one segment of said implant body, the locking element having at least two bulges corresponding to the at least two sockets, wherein said implant body and said locking element are configured to lock such that when said locking element is deflected to reach said flexed deployed state the et least two bulges of the locking element engage and lock with the at least two sockets of the implant body, said looking arrangement being effective to lock said locking element relative to said implant body in a plurality of segments, thereby retaining said implant in said flexed deployed state.

A still further aspect of the present invention is a method for deploying a medical device within a subject's body, comprising (a) providing an implant body including a plurality of segments interconnected so as to assume a straightened state and deflectable to assume a flexed deployed state, a plurality of said segments each having an engagement element; (b) providing a locking element anchored to one of at least two different segments and extending along said implant body along a direction of elongation of the implant body, the locking element having projections corresponding to each of the engagement elements; and (c) advancing the implant body into the subject's body and applying rearward tension on said locking element such that the implant body is deflected to said flexed deployed state, where said projections mate with corresponding of said engagement elements so as to lock corresponding segments in said flexed deployed state.

These and other features, aspects and advantages of the present invention will become better understood with reference to the following drawings, descriptions and claims.

BRIEF DESCRIPTION OF THE DRAWINGS

The invention is herein described, by way of example only, with reference to the accompanying drawings, wherein:

FIG. 9 is an isometric view of a tightening element engaged to an implant body, in accordance with one further embodiment of the present invention;

FIG. 10 is a side view of the tightening element of FIG. 9;

FIG. 14A is an isometric view of an implant including an implant body in a straightened state and having a locking element engaged to the implant body, in accordance with one embodiment of the present invention;

FIG. 14B is a sectional view of FIG. 14A show engagement of the locking element with projections of the implant body, in accordance with one embodiment of the present invention;

FIG. 15A is an isometric view of the implant of FIG. 14A with all but one segment in the flexed deployed state, in accordance with one embodiment of the present invention;

FIG. 15B is a sectional view of the flexed implant of FIG. 15A showing engagement of the locking element with projections of the implant body, in accordance with one embodiment of the present invention;

FIG. 16A is an isometric view of an implant in a straightened state, including an implant body and a locking element engaged to the implant body, in accordance with one further embodiment of the present invention;

FIG. 16B is an isometric view of the implant of FIG. 16A in its flexed deployed state, in accordance with one embodiment of the present invention; and FIG. 16C is a sectional view of FIG. 16B showing engagement of the bulges of the locking element with sockets of the implant body, in accordance with one embodiment of the present invention.

DETAILED DESCRIPTION OF THE INVENTION

Figure 1:
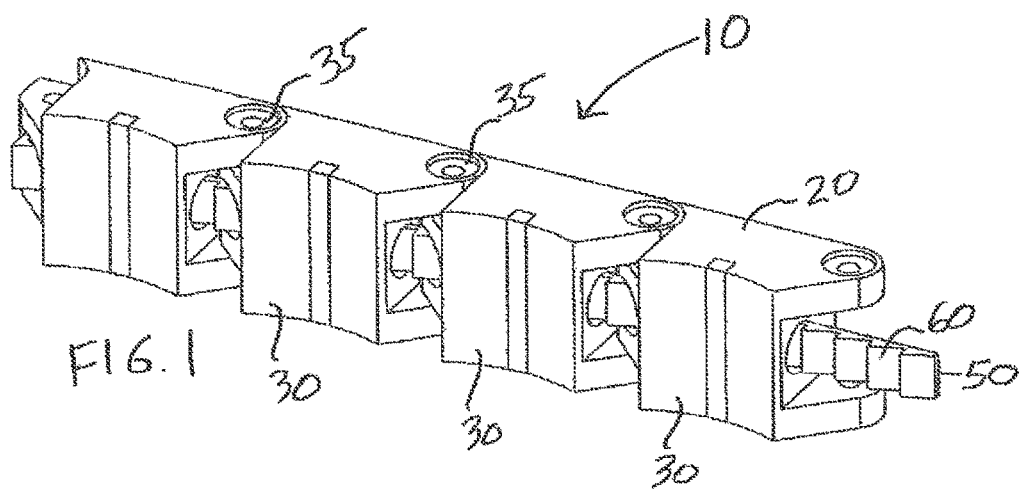
FIG. 1 is an isometric view of an implant including an implant body having a tightening element engaged to the implant body, in accordance with one embodiment of the present invention.

The present invention is an implant that may be used in the human body, lot example during spinal surgery of various types. The implant may have a stable and secure locking arrangement. The present invention also includes a corresponding method for deploying the implant through a delivery conduit. The implant may include an implant body and a locking element. The locking arrangement may include projections on the locking element that may mate with engagement elements on the segments of the implant body along the flexing portion of the implant body. The projections may be bulges, teeth, elastic tabs, etc. The engagement elements may be steps, sockets, rectangular openings, etc. As each segment flexes, the projections fall into place in the engagement dements and the implant may be unable to open inside the body in which it has been placed.

In contrast to the prior art, in which the implant locking arrangement only involves locking one segment of the implant body, the implant of the present invention may involve locking all the segments of the implant that have flexed, or in other embodiments at least two or at least three or at least one third or at least one-fourth or at least a majority of such segments. In further contrast to the prior art, in which the implant body does not have a locking arrangement that is stable, the implant of the present invention may lock in a stable and secure enough manner that the implant body may not open while in the body once it is locked in its flexed deployed state. In still further contrast to the prior art, in which the implant may lock with a single resilient tooth, the implant body of the present invention may lock with projections on segments of the implant body mating with complementary recesses on the locking element. In contrast to the prior art, the locking arrangement may comprise the mating of a plurality of bulges on multiple segments with a plurality of sockets or recesses on at least two segments, and in some embodiments on all the segments. In further contrast to the prior art, the bulge to bulge length may be smaller than the flexion region to flexion region length from one segment to its adjacent segment. As a result, bulges of the locking element that may not be in sockets in the straightened state may lock into sockets once the segments flex into the flexed deployed state. The result is extra stability of the locking arrangement.

The principles and operation of medical device locking mechanisms and methods according to the present invention may be better understood with reference to the drawings and the accompanying description.

Referring now to the drawings, FIGS. 1-5 show one embodiment of a medical device, the medical device 10 comprising an implant body 20 including a plurality of segments 30 interconnected at flexion regions 35, for example hingedly, so as to assume a straightened state and a flexed deployed state. The flexion region 35 may comprise a conventional hinge 35, an integral hinge or another structure providing the required inter-segment flexibility. As part of the locking arrangement or locking mechanism, implant body 20 may be formed with at least two engagement elements 40, each of at least two different segments, for example 30A, 30B having an engagement element 40.

Preferably, at least three segments 30 have an engagement element 40 and lock with a projection 60. In other preferred embodiments, at least a third of the segments 30 have an engagement element 40 and lock with a projection 60. In a further preferred embodiment, at least one segment 30 of each consecutive four segments 30 has an engagement element 40 and locks with a projection 60 of the elongated element 50. In other embodiments, more than half of the segments 30 have an engagement element. In one preferred embodiment, each of the segments 30 other than a distal segment 30 may have an engagement element 40 (which should be understood as not absolutely precluding the distal segment from also having an engagement element).

Medical device 10, which may be an implant 10, may also have an elongated locking element 50 that may be anchored at a distal segment of said implant body. In this regard "a distal segment" of the implant body shall be understood to refer to the most distal segment that is capable of flexing. Locking element 50 may have at least two projections 60 corresponding to the at least two engagement elements 40. Preferably, locking element 50 may have at least one projection 60 corresponding to and engaging a majority of each engagement element 40 of implant body 20 to implement the locking arrangement.

Implant body 20 and locking element 50 may be configured such that tension applied to tightening element 50 tends to bias implant body 20 from its straightened state to its flexed deployed state. Elongated locking element 50 may pass along a channel extending along implant body 10.

Implant body 20 and elongated locking element 50 may be configured to lock securely and with stability to prevent implant 10 from opening once emplaced in its flexed state in the spine or other part of the body. This locking may be such that when locking element 50 is deflected to reach the flexed deployed state (as part of implant body 20), each successive segment 30 of implant body 20 may flex and the at least two projections 60 of elongated locking element 50 may engage and lock with the at least two engagement elements 40 of implant body 20. Each locking segment 30 may remain locked after one or more successive segments flex and lock. Accordingly, the locking arrangement is effective to lock the locking element 50 relative to implant body 20, thereby retaining implant 10 in said flexed deployed state in the body.

By way of example, each of at least two or at least three or at least one-third of the segments or at least one-fourth of the segments or at least the majority of the segments or at least one out of every four consecutive segments, of said implant body may for example be formed with at least one engagement element so as to lock with the locking element. Further, the locking element may have a projection corresponding to and engaging each of the engagement elements of the implant body to provide said locking arrangement. Alternatively, locking element 50 may have a multiplicity of projections 60 but may have less than one projection for each engagement element 40 of implant body 20. In some preferred embodiments, the locking element 50 may have many more projections than there are engagement elements of the implant body. For example every fourth projection 60 may lock with an engagement element. In some cases, moreover, each segment 30 may have multiple engagement elements 40.

The projections 60 and engagement elements 40 may encompass a variety of shapes including cross-sectional shapes. In general, engagement elements 40 of implant body 20 are broadly defined to include a step, a slot or any shape that can receive and "catch" the projection 60 (i.e. a bulge, tooth or elastic tab) of locking element 50. In the embodiment of FIGS. 1-5, engagement elements 40 may be described as steps 40 that may catch teeth 60 projecting from locking element 50. The structure and dimensions of projections 60 may be chosen according to the mechanical properties of the materials used to provide sufficient resilience and secure locking, and in accordance with considerations of biocompatibility. The corresponding engagement elements may be implemented as any suitably positioned element or recess, for example an upward projection or a recessed notch, or a combination thereof.

Figure 6:
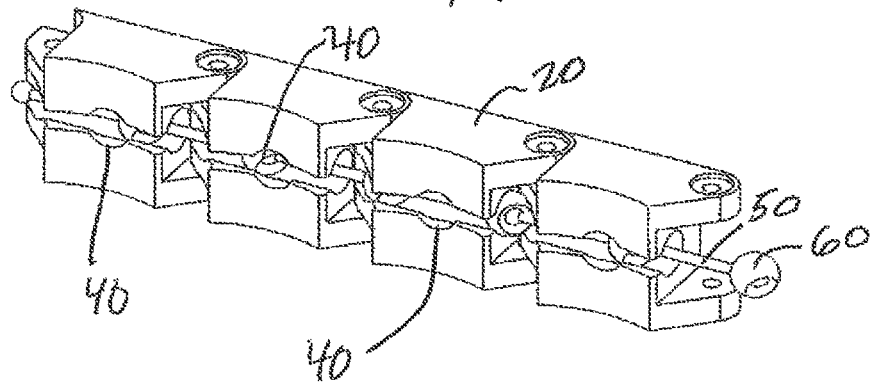
FIG. 6 is an isometric view of an implant in a straightened state, including an implant body and a tightening element engaged to the implant body, in accordance with one further embodiment of the present invention.
Figure 7:
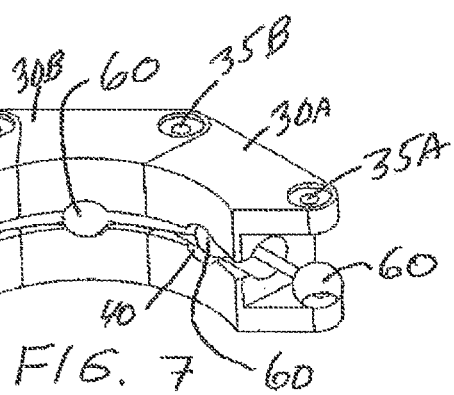
FIG. 7 is an isometric view of the implant of FIG. 6 in its flexed deployed state, in accordance with one embodiment of the present invention.
Figure 8:
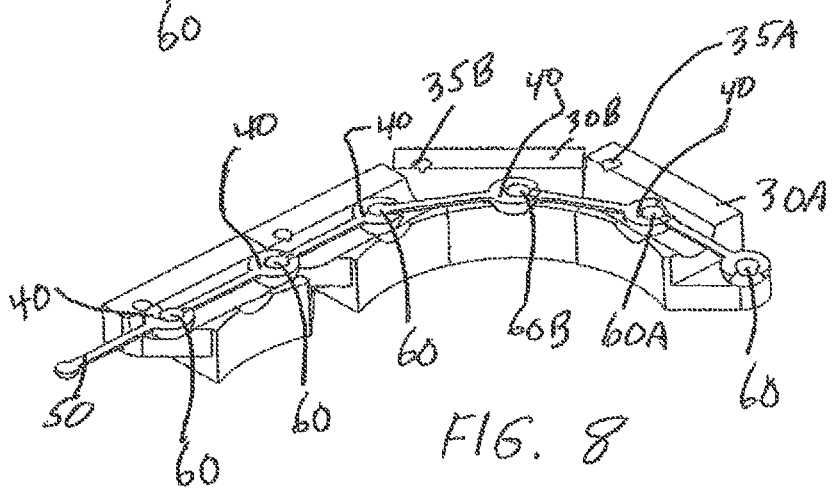
FIG. 8 is a partial view of FIG. 7 broken away to show engagement of the bulges of the tightening element with sockets of the implant body, in accordance with one embodiment of the present invention.

In FIGS. 6-8, the engagement elements may be described as sockets 40 and the projections may be described as bulges 60. The term "bulge" is not limited to a rounded bulge, even though in some embodiments, such as FIGS. 6-8, bulges 60 may be spherical. Similarly, the term "socket" is not necessarily referring to a rounded socket, although in FIGS. 6-8 sockets 40 are rounded. Furthermore, it is contemplated that projections 60, including bulges 60, could be solid or hollow.

In the embodiment shown in FIGS. 9-12, the projections 60 may be described as elastic tabs 60 and engagement elements 40 may be complementary recesses 40. For example, each segment 30 may have at least one complementary recess and at least one elastic tab of tightening element 60 may lock with the at least one complementary recess 40 of each segment 30 as each segment flexes in the flexed deployed state.

In FIGS. 9-12, implant body 200 may have segments 220 and a zipper-like locking element 210 that may be rigidly attached to a distal segment 220 and that may be engaged in all segments of the implant 200. The proximal end of locking element 210 can be pulled in a rearward direction relative to implant body 200. Implant body 200 may have recesses 222 or slots. Locking element 210 may be a strip and may be implemented for example using metal (e.g., Nitinol, Stainless Steel) or plastic (e.g., PEEK, UHMWPE), and has a series of elastic tabs 212 which may latch onto the corresponding engagement elements 222 of implant body 200.

Figure 11:
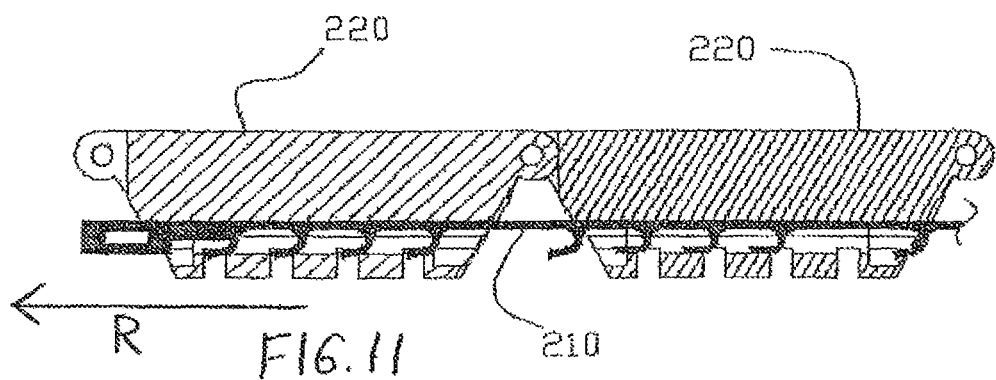
FIG. 11 is a sectional view of two segments of the locking mechanism of the implant of FIGS. 9-10 with the implant in a straightened state, in accordance with embodiment of the present invention.
Figure 12:
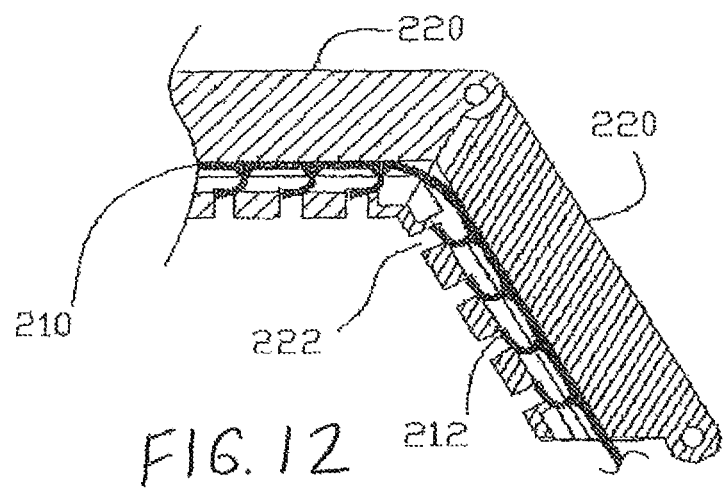
FIG. 12 is a sectional view of the two segments of the locking mechanism of the implant of FIGS. 9-10 with the implant in a flexed deployed state, in accordance with one embodiment of the present invention.

FIGS. 11-12 show the actual locking mechanism in between two adjacent segments 220. FIG. 11 shows two segments 220 in the straightened state of implant body 200 whereby a notch or opening (which is V-shaped in this embodiment) appears between each of the two consecutive segments 220. Once locking element 210 is pulled in the rearward direction in accordance with arrow R in FIG. 11) relative to segments 220, segments 220 rotate due to the offset between an axis of segments 220 and a channel through which the tightening element 210 passes. As a result of the rotation, segments 220 now close upon each other internally as shown in FIG. 12. As also shown in FIG. 12, the elastic tabs 212 are locked inside slots 222 and as a result segments 220 are attached with each other and are strongly locked.

In some embodiments, a tensioning element separate from locking element 50 (or 210) may be used to pull the implant body in a rearward direction and induce flexing of its segments 30. In that case the tensioning element would be used to first cause the device 10 to flex. Then, locking element 50 may be pulled to lock the device by mating projections 60 with engagement elements 40.

The locking mechanism of the present invention in any of the above embodiments may be further enhanced by using multiple locking elements (50 or 210). In this case, multiple projections of implant body (200 or 20) within a segment may engage and lock with multiple engagement elements (222 or 40) on each segment (220 or 30) of implant body. In one example, the multiple locking elements may be side by side strips of material.

Figure 2:
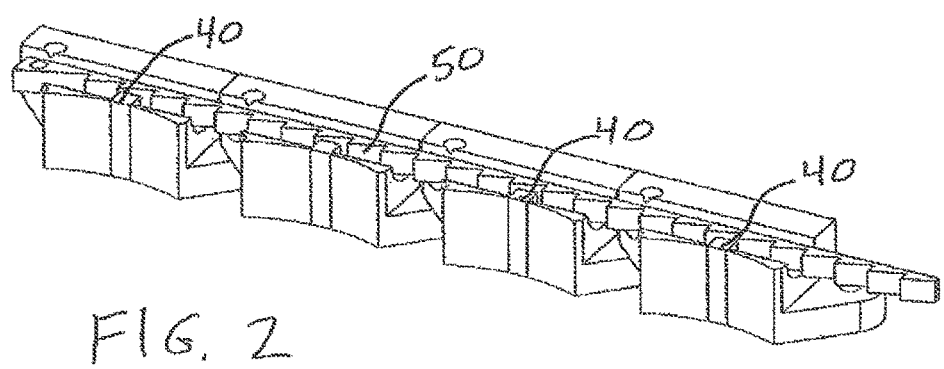
FIG. 2 is a partial view of FIG. 1 broken away to show engagement of the tightening element with projections of the implant body, in accordance with one embodiment of the present invention.
Figure 3:
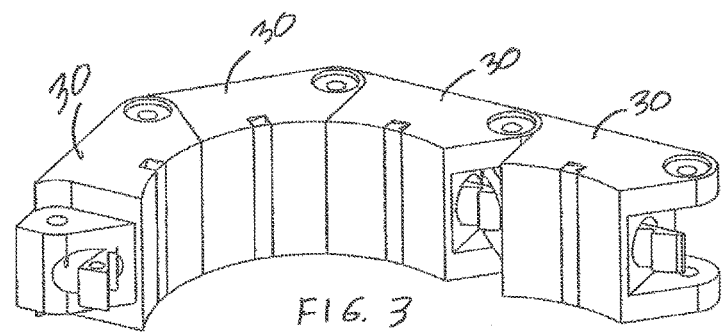
FIG. 3 is an isometric view of the implant of FIG. 1 with all but one segment in the flexed deployed state, in accordance with one embodiment of the present invention.
Figure 4:
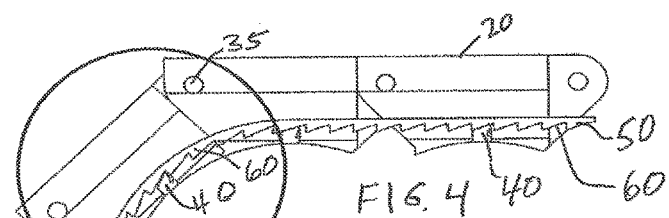
FIG. 4 is a partial side view of the flexed implant of FIG. 3 broken away to show engagement of the tightening element with projections of the implant body, in accordance with one embodiment of the present invention.
Figure 5:
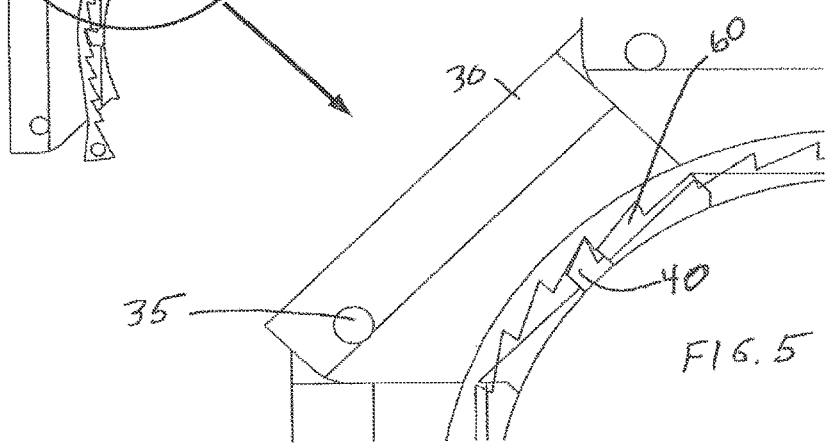
FIG. 5 is an enlarged view of the region of FIG. 4 denoted by the circle showing a locking arrangement of the implant, in accordance with one embodiment of the present invention.

The medical device 10 of the present invention may further include a conduit sized to receive the medical device 10, for example when the medical device 10 is in its straightened shape, and to maintain the implant body 20 in the straightened state. The conduit may be straight in shape and may be close-fitting to the external shape of implant 10. Although the conduit is not shown in FIGS. 1-3 herein, an example of a conduit that may be used for an implant 10 of the present invention is shown in FIGS. 2-3 of publication WO 2006/072941 published 13 Jul. 2006. Implant body 20 and locking element 50 may be configured to lock such that when said locking element is deflected to reach the flexed deployed state each successive segment flexes and the projections of the locking element engage and look with the engagement elements of the implant body. In FIG. 6, when implant body is in a straightened state, projections 60 of locking element 50, which in FIG. 6 may be bulges 60, may not necessarily be situated in or engaged to, and indeed likely are not situated in or engaged to, engagement elements 40, which in FIG. 6 may be described as sockets 40, of implant body 20. In FIG. 7, only those segments 30 that have already flexed (30A, 30B) may have their engagement elements or sockets 40 occupied by bulges 60. Further, in FIG. 8, it is more easily seen that bulges 60 are in sockets 40 for flexed segments 30. A careful inspection of FIGS. 6-8 and in particular FIG. 8 reveals that in the implant 10 a length from a bulge 60A to the nearest adjacent bulge 60B may be shorter than a length from a flexion section 35A of a segment 30A, to a flexion section 35B of an adjacent segment 30B. It should be noted that in the embodiment of FIGS. 6-8 the length from bulge 40 to bulge 40 (i.e. to adjacent bulge 60) may be substantially uniform and similarly the length from socket to socket (i.e. to adjacent socket 40) may be substantially uniform. However, in an embodiment in which the medical is helical or non-planar or where a non-uniform curvature of the medical device is required, these distances may not be uniform, although socket to socket distance may still match bulge to bulge distances at flexing segments.

It is noted that as successive segments 30A, 30B, 30C, 30D flex, the roughly arcuate shape of tightening element 50 may span a smaller are than the roughly arcuate shape of the hinges 35 of implant body 20. This is because in a flexed deployed state, tightening element 50 of implant 10 is inward of most of implant body 20, and in particular is inward of hinges 35. In this regard, "inward" is described relative to closeness to the center of the arc/circle made by the arcuate form of implant 10 (locking element 50 and implant body 20) in its flexed deployed state. Accordingly, in the straightened state at least some of the bulges of the locking element may be situated in portions of hinges outside the sockets and in the flexed deployed state the bulges of the locking element are situated in the sockets of flexed segments. Each segment 30 that has flexed may have a bulge 60 that is engaged to its corresponding socket. As seen from FIG. 8, in the flexed deployed state, every flexed segment that has a socket also has a bulge situated therein.

Although the drawings illustrate embodiments in which the implant flexes in a two dimensional plane so that the direction of elongation of implant 10 may be said to be substantially co-planar with hinges and perpendicular to the hinges 35 in that plane, the present invention is equally applicable to nonplanar or helical forms of the implant 10, such as where a direction of elongation of the implant running from a distal flexing segment to a proximal flexing segment in the flexed deployed state is not perpendicular to the hinges of the segments that flex. An example of a helical configuration of implant without the locking arrangement of the present invention is described in PCT patent application publication no. WO 2008/072941 of Applicant published 13 Jul. 2006 (see FIGS. 9A, 9B, and 10 and page 17 therein), which publication is hereby incorporated by reference in its entirety. This publication also describes general features of segments 30 and implant 10 although without the stable and secure locking arrangement of the present invention.

Figure 13:
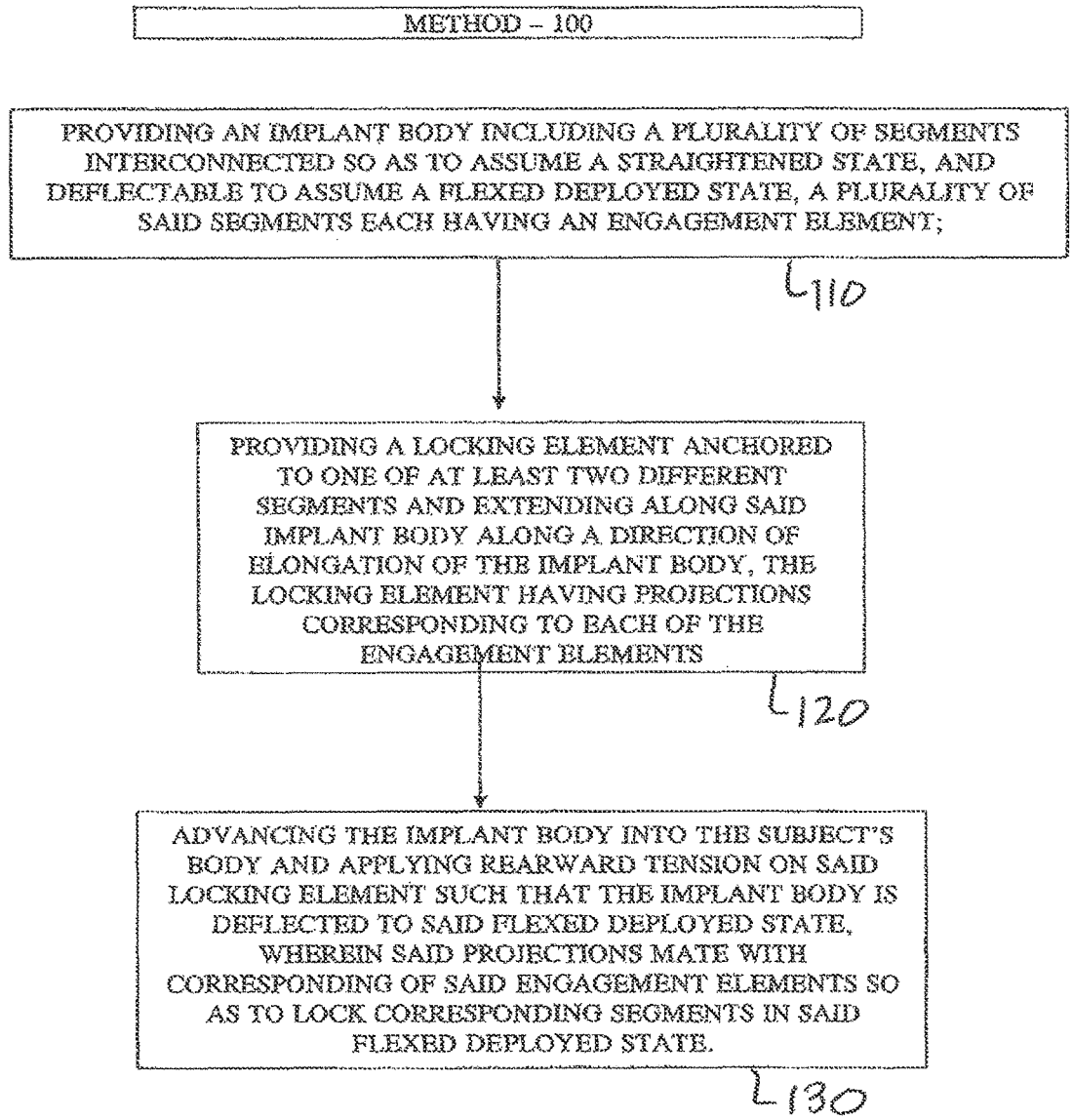
FIG. 13 is a flow chart showing a method of the present invention.

As seen in FIG. 13, the present invention may also be described as a method 100 for deploying an implant within a subject's body. Method 100 may comprise a first step 110 of providing an implant body including a plurality of segments hingedly interconnected so as to assume a straightened state, and deflectable to assume a flexed deployed state, a plurality of said segments each having an engagement element. In a further step 120, method 100 may involve providing a locking element anchored to a distal segment, the locking element extending along the implant body along a direction of elongation of the implant body. The locking element may have projections corresponding to each of the engagement elements of the implant body. In step 130 at method 100, the implant body may be advanced into the subject's body. Further, rearward tension may be applied on the locking element such that the implant body is deflected to the flexed deployed state. The projections may thereby mate with corresponding engagement elements so as to lock corresponding segments in the flexed deployed state. Some versions of method 100 may also include a step of releasing the locking element from its anchor and pulling out the locking element from the medical device.

Structurally, the flexion regions hinges 35 between segments 30 may be implemented in a wide range of ways. Most preferably, the interconnection between segments 30 may be a hinged interconnection, which may be is achieved by integral hinges 36 integrally formed with segments 30 either during an injection or molding process, or through cutting out of recesses from an initial block of material. The recesses may be V-shaped notches, parallel sided, or any other suitable form. Most preferably, V-shaped slots are used so that the curved deployed form of the implant has the spaces between the segments essentially closed. However, alternative implementations, such as where the hinged interconnection is provided by a separate structure 39 (e.g., a "backbone") to which segments 30 are attached, also fall within the scope of the present invention. In the latter case, the backbone may be of a different material from the segments themselves, chosen according to the intended application. Options for materials for the backbone include, but are not limited to, metallic materials, various plastics and other polymers and fabrics.

The flexed deployed state is also referred to as the curved deployed form. However, the "flexing" referred to herein does not necessarily involve actual bending of the segments, although there could be such bending in some embodiments. Moreover, the curved deployed form should not be understood as necessarily representing a perfect curve, particularly when examined through relatively small numbers of segments. Accordingly, the flexed deployed form, which is called the curved deployed form of implant body 10 is preferably a roughly arcuate form, and it may typically extend around about 180 degrees to form what appears as a substantially "U-shaped" form. The term "U-shaped" is used herein to refer generically to any shape which has a medial portion which turns through roughly 180 degrees (i.e., 180 degrees plus or minus 20 degrees) without specifying in detail the shape, geometry or extent of the two side portions. (It is noted parenthetically that the letter "u" itself is asymmetric in many typefaces.). It will be appreciated that the above descriptions are intended only to serve as examples, and that many other embodiments are possible within the scope of the present invention as defined in the appended claims.

What is claimed is:

1. A medical device comprising:
  (a) an implant body including a backbone and including a plurality of segments interconnected at least by virtue of being commonly attached to the backbone, so that the implant body assumes a straightened state and a flexed deployed state, a segment of said plurality of segments having an engagement element; and
  (b) an elongated locking element anchored at one segment of said implant body, the locking element having a projection corresponding to the engagement element,
  wherein said implant body and said locking element are configured to lock, such that when said locking element is deflected to reach said flexed deployed state of the implant body, the projection of the locking element engages and locks with the engagement element of the implant body to lock said locking element relative to said implant body, thereby retaining said medical device in said flexed deployed state,
    wherein at least one additional segment of said implant body has an additional engagement element and said elongated locking element has at least one additional projection that engages and locks with the additional engagement element when said at least one additional segment of said implant body flexes, said implant body and said locking element being configured such that, when said implant body is deflected, each successive segment of said implant body flexes, and projections engage said engagement elements only for those segments that have already flexed.

2. The medical device of claim 1, wherein each of at least three of the segments of said implant body are formed with at least one engagement element from among the engagement element and the at least one additional engagement element, and the locking element has a projection corresponding to and engaging at least one of the engagement elements of the implant body from among the engagement element and the at least one additional engagement element to provide said locking arrangement.

3. The medical device of claim 1, wherein each of at least one-third of the segments of said implant body are formed with at least one engagement element from among the engagement element and the at least one additional engagement element, and the locking element has a projection corresponding to and engaging each of the engagement elements of the implant body from among the engagement element and the at least one additional engagement element to provide said locking arrangement.

4. The medical device of claim 1, wherein in any group of four consecutive segments, at least one out of the four consecutive segments has an engagement element from among the engagement element and the at least one additional engagement element, and locks with a corresponding projection of the locking element.

5. The medical device of claim 1, wherein each of the segments of said implant body other than a distal segment is formed with at least one engagement element from among the engagement element and the at least one additional engagement element, and the locking element has a projection corresponding to and engaging at least two of the engagement elements of the implant body from among the engagement element and the at least one additional engagement element.

6. The medical device of claim 1, wherein a majority of segments of the plurality of segments are formed with at least one engagement element from among the engagement element and the at least one additional engagement element, and the locking element has a projection corresponding to each of the at least one engagement element.

7. A medical device comprising:
(a) an implant body including a backbone and including a plurality of segments interconnected at least by virtue of being commonly attached to the backbone, so that the implant body assumes a straightened state and a flexed deployed state, a segment of said plurality of segments having an engagement element; and
(b) an elongated locking element anchored at one segment of said implant body, the locking element having a projection corresponding to the engagement element, wherein said implant body and said locking element are configured to lock, such that when said locking element is deflected to reach said flexed deployed state of the implant body, the projection of the locking element engages and locks with the engagement element of the implant body to lock said locking element relative to said implant body, thereby retaining said medical device in said flexed deployed state,
wherein:
the engagement elements of the implant body comprise at least two sockets, each of at least two different segments having a socket; and the projections of the locking element comprise at least two bulges, the at least two bulges corresponding to the at least two sockets,
wherein said implant body and said locking element are configured to lock such that when said locking element is deflected to reach said flexed deployed state the at least two bulges of the locking element engage and lock with the at least two sockets of the implant body by said at least two bulges occupying said at least two sockets, and such that said locking element is locked relative to said implant body in a plurality of segments.

8. The medical device of claim 7, wherein each of at least half of the segments of said implant body is formed with at least one socket and wherein the tightening element has a bulge corresponding to substantially all of the sockets to provide said locking arrangement.

9. The medical device of claim 7, wherein a length from bulge to nearest adjacent bulge is shorter than a length from a flexion region of a segment to a flexion region of an adjacent segment.

10. The medical device of claim 7, wherein the length from bulge to bulge is substantially uniform and wherein the length from socket to socket is substantially uniform.

11. The medical device of claim 7, wherein in the straightened state at least some of the bulges of the tightening element are situated in portions of flexion regions outside the sockets and in the flexed deployed state the bulges of the tightening element are situated in the sockets of flexed segments.

12. The medical device of claim 7, wherein in the flexed deployed state, every flexed segment that has a socket also has a bulge situated therein.

13. The medical device of claim 7, wherein the medical device is helical.

14. The medical device of claim 7, further including a conduit sized to receive said medical device and to maintain said implant body in said straightened state.

15. The medical device of claim 7, wherein the bulges and the sockets are spherical.

16. A method for deploying a medical device within a subject's body, comprising:
providing an implant body including a backbone and a plurality of segments, the segments interconnected at least by virtue of being commonly attached to the backbone, so that the implant assumes a straightened state and a flexed deployed state, each of the interconnected segments having an engagement element;
providing a locking element anchored to one of at least two different segments of the plurality of segments and extending along said implant body along a direction of elongation of the implant body, the locking element having projections corresponding to each of the engagement elements; and
advancing the implant body into the subject's body and applying rearward tension on said locking element such that the implant body is deflected to said flexed deployed state,
wherein said projections mate with corresponding one of said engagement elements so as to lock corresponding segments in said flexed deployed state, such that, when said implant body is deflected, each successive segment of said implant body flexes, and projections engage said engagement elements only for those segments that have already flexed,
further comprising releasing the locking element from an anchor and pulling out the locking element from the implant body.

17. A medical device comprising:
an implant body including a plurality of segments interconnected so as to assume a straightened state of the implant body and a flexed deployed state of the implant body, one of said segments having an engagement element; and an elongated locking element anchored at one segment of said implant body, the locking element having a projection corresponding to the engagement element,
wherein said implant body and said locking element are configured to lock, such that when said locking element is deflected to reach said flexed deployed state of the implant body, the projection of the locking element engages and locks with the engagement element of the implant body to lock said locking element relative to said implant body, thereby retaining said medical device in said flexed deployed state,
wherein:
(a) the engagement element and additional engagement elements of the implant body comprise at least two sockets, each of at least two different segments having a socket; and
(b) the projections of the locking element comprise at least two bulges, the at least two bulges corresponding to the at least two sockets,
wherein said implant body and said locking element are configured to lock such that when said locking element is deflected to reach said flexed deployed state the at least two bulges of the locking element engage and lock with the at least two sockets of the implant body by said at least two bulges occupying said at least two sockets, and such that said locking element is locked relative to said implant body in a plurality of segments.

18. The medical device of claim 17, wherein at least one additional segment of said implant body has an additional engagement element and said elongated locking element has at least one additional projection that engages and locks with the additional engagement element when said at least one additional segment of said implant body flexes, said implant body and said locking element being configured such that, when said implant body is deflected, each successive segment of said implant body flexes, and projections engage said engagement elements only for those segments that have already flexed.

19. A medical device comprising:
an implant body including a plurality of segments, the plurality of segments configured to be commonly attached to a backbone that engages the medical device, and in being so attached the plurality of segments being interconnected such that the implant body assumes a straightened state and a flexed deployed state, one of said segments having an engagement element; and
an elongated locking element anchored at one segment of said implant body, the locking element having a projection corresponding to the engagement element,
wherein said implant body and said locking element are configured to lock, such that when said locking element is deflected to reach said flexed deployed state of the implant body, the projection of the locking element engages and locks with the engagement element of the implant body to lock said locking element relative to said implant body, thereby retaining said medical device in said flexed deployed state,
wherein at least one additional segment of said implant body has an additional engagement element and said elongated locking element has at least one additional projection that engages and locks with the additional engagement element when said at least one additional segment of said implant body flexes, said implant body and said locking element being configured such that, when said implant body is deflected, each successive segment of said implant body flexes, and projections engage said engagement elements only for those segments that have already flexed.

* * * * *